(12) United States Patent
Pajunk et al.

(10) Patent No.: US 7,883,512 B2
(45) Date of Patent: Feb. 8, 2011

(54) APPARATUS FOR THE APPLICATION OF BONE CEMENT

(75) Inventors: Heinrich Pajunk, Geisingen (DE); Horst Pajunk, Geisingen (DE)

(73) Assignee: Pajunk Ohg Besitzverwaltung, Geisingen (DE)

( * ) Notice: Subject to any disclaimer, the term of this patent is extended or adjusted under 35 U.S.C. 154(b) by 1567 days.

(21) Appl. No.: 11/038,798

(22) Filed: Jan. 20, 2005

(65) Prior Publication Data

US 2005/0124997 A1    Jun. 9, 2005

Related U.S. Application Data

(63) Continuation of application No. 09/865,109, filed on May 24, 2001, now abandoned.

(30) Foreign Application Priority Data

May 25, 2000   (DE)   ................ 100 25 898
Dec. 22, 2000   (DE)   ................ 100 64 202

(51) Int. Cl.
*A61B 17/56*     (2006.01)

(52) U.S. Cl. ...................................... 606/94

(58) Field of Classification Search ............. 606/92–94, 606/99; 604/38, 68, 97.02, 124, 125, 155, 604/184, 187, 188, 211, 218, 224, 235
See application file for complete search history.

(56) References Cited

U.S. PATENT DOCUMENTS

| | | | |
|---|---|---|---|
| 2,711,733 A | 6/1955 | Jacoby, Jr. | |
| 3,628,524 A | 12/1971 | Jamshidi | |
| 4,576,152 A | 3/1986 | Mueller et al. | |
| 4,583,974 A | 4/1986 | Kokernak | |
| 4,655,749 A * | 4/1987 | Fischione | 604/97.03 |
| 4,832,692 A | 5/1989 | Box et al. | |
| 4,940,459 A | 7/1990 | Noce | |

(Continued)

FOREIGN PATENT DOCUMENTS

DE       601 17 524 T2    8/2006

(Continued)

OTHER PUBLICATIONS

Imad Al-Assir et al., "Percutaneous Vertebroplasty: A Special Syringe for Cement Injection", American Journal Neuroradiol, vol. 21, Jan. 2000, pp. 159-161.

(Continued)

*Primary Examiner*—Eduardo C Robert
*Assistant Examiner*—Mary Hoffman
(74) *Attorney, Agent, or Firm*—Fitch, Even, Tabin & Flannery (57) ABSTRACT

An apparatus for the application of bone cement is described having a housing that comprises a cylinder for the reception of the bone cement. The apparatus further comprises a piston arranged in a longitudinally displaceable manner in the cylinder, by which the bone cement can be pressed out of an exit aperture formed in the cylinder, wherein the piston is longitudinally displaceable in the cylinder by a screw movement to apply the bone cement under high pressure. The apparatus can be switched between the displacement of the piston by the screw movement and a direct displacement in the longitudinal direction without a screw movement. Furthermore, a cannula for such an apparatus is described.

15 Claims, 5 Drawing Sheets

U.S. PATENT DOCUMENTS

| | | |
|---|---|---|
| 5,051,482 A | 9/1991 | Tepic |
| 5,137,514 A | 8/1992 | Ryan |
| 5,398,483 A | 3/1995 | Smith et al. |
| 5,507,727 A | 4/1996 | Crainich |
| 6,048,346 A | 4/2000 | Reiley et al. |

FOREIGN PATENT DOCUMENTS

| | | |
|---|---|---|
| EP | 1 074 231 A1 | 2/2001 |
| EP | 1074231 | 2/2001 |
| FR | 577367 | 9/1924 |
| WO | 94/23639 A1 | 10/1994 |
| WO | 95/02363 A1 | 1/1995 |
| WO | 99/02214 A1 | 1/1999 |
| WO | WO 99/49819 | 10/1999 |
| WO | 00/09024 A1 | 2/2000 |

OTHER PUBLICATIONS

Jerosch et al., "Perkutane vertebrale Augmentation (PVA) bei osteoporotischen Wirbelkorpern-eine experimentelle Untersuchung" Biomed. Technik, vol. 44, 1999, pp. 190-193.

"Kanule", Extract from Brockhaus Encyclopedia Online, Brockhaus AG, 1 page, 2005-2007.

"Ballonkatheter", Extract from Brockhaus Encyclopedia Online, Brockhaus AG, 1 page, 2005-2007.

European Search Report (and English translation thereof), Oct. 30, 2006, relating to corresponding EP Application No. 06017467.9.

"Römpp Chemie Lexikon", vol. 9, Stuttgart and New York, 1990.

Amir R. Dehdashti et al., "PMMA Cementoplasty in Symptomatic Metastatic Lesions of the S1 Vertebral Body", CardioVascular and Interventional Radiology, 23 (2000), No. 3, pp. 235-237.

Rey Osorio et al., U.S. Appl. No. 60/194,685, filed Apr. 5, 2000.

\* cited by examiner

APPARATUS FOR THE APPLICATION OF BONE CEMENT

This application is a continuation of U.S. application Ser. No. 09/865,109, filed May 24, 2001 now abandoned which claims the benefit of German Application No. 100 25 898.0 filed May 25, 2000 and German Application No. 100 64 202.0 filed Dec. 22, 2000.

FIELD

The present invention relates to an apparatus for the application of bone cement having a housing which comprises a cylinder for the reception of the bone cement and having a piston arranged longitudinally displaceably in the cylinder by which the bone cement can be pressed out of an exit aperture formed in the cylinder, with the piston for the application of the bone cement under high pressure being longitudinally displaceable by a screw movement in the cylinder. A cannula for an apparatus for the application of bone cement having an aperture formed at the distal end and a coupling section provided at the proximal end for coupling to the application apparatus is further described.

BACKGROUND

Application apparatuses of this kind are used when bone structures break down or become brittle, for example due to bone cancer or osteoporosis. With appropriate apparatuses, the application of bone cement directly into the affected bone structures is possible, whereby these are solidified.

A plurality of demands must be considered during application. On the one hand, the filling of the application apparatus and the application into the affected bone structures must take place very rapidly, within a few minutes, since the bone cements usually used begin to harden 6 to 7 minutes after mixing. On the other hand, the bone cement must be applied at a very high pressure, since otherwise sufficient penetration of the bone structures is not ensured. Finally, the application of the bone cement must be easily controllable, since a misdirecting of the bone cement can lead to irreversible damage, for example to nerves, particularly during application in the region of the spinal column.

OBJECTS

It is an object of the present invention to provide an apparatus for the application of bone cement and a cannula for an application apparatus, with which the application can be carried out in a short time, with the required high pressure being able to be built up simultaneously and with a control capability of the applied bone cement being possible.

This object is satisfied in accordance with the invention, starting from an application apparatus of the kind initially named, by the apparatus being switchable between the displacement of the piston by the screw movement and a direct displacement in the longitudinal direction without a screw movement. A cannula in accordance with the invention is characterized in that the distal end of the cannula is formed asymmetrically with a tip disposed to the side of the central axis and in that laterally outwardly projecting handling elements are provided at the proximal end of the cannula with which the cannula can be both turned around its longitudinal axis and displaced along its longitudinal axis.

SUMMARY

Within the framework of this application, the term "proximal" is used in the meaning of "disposed toward the body of the physician". The term "distal" is used accordingly to mean "disposed remote from the body of the physician".

The switchability of the application apparatus in accordance with the invention means that it is possible, for example, for the filling of the cylinder to take place in a very short time by a loading movement of the piston, i.e. by a direct displacement of the piston in the longitudinal direction. The liquid cement present in the cylinder can, vice versa, subsequently be applied in a short time by a direct displacement of the piston for so long until the counter pressure which is created becomes so large that it can no longer be overcome by the direct advance movement. At this moment, the application apparatus is switched to a mode "displacement of the piston by screw movement", since a substantially greater pressure can be exerted on the piston, and thus on the bone cement to be applied by the screw movement, than with a direct advance movement.

The advance speed is actually much lower with the screw movement than with a direct displacement in a longitudinal direction; since, however, both the filling of the cylinder and the application of the liquid bone cement can take place in a very short time until the described high pressure is reached due to the direct longitudinal displacement of the piston, there is normally still sufficient time available at that moment when it becomes necessary to switch to the further application by a screw movement to end the application before the bone cement starts to harden.

A further advantage of the application apparatus formed in accordance with the invention lies in the fact that the high pressure built up during the application with a screw movement can be built up very fast, i.e. within fractions of a second. This is required, for example, when a misdirecting of the bone cement is recognized during the observation, for example at a fluoroscope, of the bone cement exiting the cannula. In this case, a simple switching of the apparatus to the direct longitudinal displaceability of the piston allows the piston to be pushed back due to the high pressure and thus the pressure to be automatically reduced. In this way, the misdirected exit of the bone cement from the distal end of the cannula is stopped directly.

In accordance with an advantageous embodiment of the invention, the piston comprises an engaging section with a screw thread which engages into a cooperating toothed arrangement provided at the housing so that the longitudinal displacement of the piston takes place when the engaging section is turned. The cooperating toothed arrangement can in particular be formed as a rack. In this way, a very simple, low-cost and reliably working design of an application device in accordance with the invention can be achieved. In particular, a direct displacement in the longitudinal direction is automatically prevented in the operating mode "displacement by screw movement" by the toothed arrangements, which engage into one another, so that the increase of the applied pressure achieved with each revolution is automatically ensured.

In accordance with a further preferred embodiment of the invention, the screw thread and the cooperating toothed arrangement can be uncoupled, with the cooperating toothed arrangement advantageously being able to be moved substantially perpendicular to the direction of displacement of the piston between a locking position and releasing position for the uncoupling. A simple and fast switch from the operating state "displacement by screw movement" into the operating state "direct displacement in the longitudinal direction" and back is made possible by this design, by, for example, the cooperating toothed arrangement being displaced into the release position via an actuating unit attached to the housing.

The cooperating toothed arrangement is advantageously pressed against the screw thread under bias. It is ensured in this way that the built-up pressure is automatically ensured for so long until the cooperating toothed arrangement is moved against the bias. This bias can be effected for example by a loading of a spring.

In accordance with a further advantageous embodiment of the invention, the cooperating toothed arrangement grips around the screw thread regionally, in particular free of undercutting. An enlarged contact surface between the teeth of the cooperating toothed arrangement contacting one another under high pressure and the thread section of the screw thread is achieved by a regional gripping around of the screw thread so that the stability of the apparatus is increased. The gripping around free of undercutting ensures that a simple uncoupling of the screw thread and the cooperating toothed arrangement is still possible, for example by a simple lateral displacement of the cooperating toothed arrangement.

The piston is preferably substantially freely longitudinally displaceable in the cylinder in the uncoupled state. The free displaceability of the piston is essentially only impaired by a seal which is usually provided for sealing between the piston circumference and the inner wall of the cylinder.

In accordance with a further advantageous embodiment of the invention, the tooth flanks of the cooperating toothed arrangement and/or the flanks of the thread section of the screw thread which abut one another during the application of the bone cement under pressure form an angle of less than or equal to 90° with the longitudinal axis of the engaging section extending parallel to the direction of displacement. It is ensured by his special formation of the flanks that no over-latching of individual teeth occurs—such as can be the case with normal, chamfered flanks where the angle between the longitudinal axis of the engaging section is greater than 90°—even when very high pressures are used. If the angle amounts to substantially equal to 90°, the cooperating toothed arrangement can be displaced by a displacement movement perpendicular to the direction of movement of the engaging section for the uncoupling from the screw thread. If the angles are less than 90°, uncoupling is possible by a corresponding displacement of the cooperating toothed arrangement obliquely to the longitudinal axis of the engaging section.

The piston and the engaging section are preferably formed in one piece. With a one-piece formation, it must be ensured that the piston is rotatable in the cylinder in order to allow the screwing of the engaging section in this manner. In this embodiment, the longitudinal displacement of the piston is thus directly achieved by screwing in the piston.

It is also possible for the piston to be formed in two parts so that the engaging section forms a separate part. In this case, both parts are connected to one another, in particular in a manner rotatable against one another. In this embodiment, it is possible for only the engaging section to be rotated in the screw movement, while the piston is forwardly displaced inside the cylinder without rotation by the forward-screwing engaging section. While in this case the cross-section areas of the piston and the cylinder are complementary to one another, but can be of any shape in principle; for example, they can have an oval or polygonal shape, with the single-piece design of the piston and the engaging section, the cylinder is usually formed as a circular cylinder in order to allow a rotation of the piston in the cylinder together with the engaging section in this manner.

In accordance with a further advantageous embodiment of the invention, a cannula is fastenable to the exit aperture of the cylinder. This cannula is preferably releasably fastened since, in this way, the cannula can be introduced and positioned in the patient in a first process step without an application apparatus, while the application apparatus can be filled with the liquid bone cement in a second process step only after the successful positioning, for example via a loading cannula likewise attachable to the exit aperture. After the removal of the loading cannula, the application apparatus can subsequently be fastened to the already inserted injection cannula and the bone cement applied in the previously described manner.

The cannula in accordance with the invention has the advantage that as a result of its asymmetrical tip and also the laterally outwardly projecting handling elements, an exact positioning can already be made during the introduction of the cannula. Conventional cannulae have a symmetrical tip and cannot be altered with respect to their direction of introduction during introduction. With the cannula of the invention, however, the asymmetrical tip can be positioned by a rotation of the partly introduced cannula via the laterally outwardly projecting handling elements such that a movement of the cannula in the desired direction is achieved during the further introduction. The cannula will always deviate slightly in the lateral direction to which the tip is just disposed due to the preceding asymmetrical tip. By a repeated alternate introduction and rotation, an improved positioning and a subsequent correcting of the position is thus still possible during the introduction with the cannula formed in accordance with the invention.

It is furthermore possible with the cannula of the invention to allow turning or shearing off of the bone cement still hardening inside the cannula from the bone cement applied into the bone structure by turning the cannula still located in the body around its longitudinal access via the handling elements after the hardening of the applied bone cement. It is thereby ensured that the bone cement located inside the cannula remains in it when it is pulled out and is reliably removed from the tissue together with it.

The edge of the cannula forming the border of the aperture is preferably ground as a cutting edge. A reliable shearing off of the material disposed inside the cannula is thereby also ensured with a completely hardened bone cement.

In accordance with a further advantageous embodiment of the invention, the penetration surface of the aperture extends obliquely to the longitudinal axis of the cannula. The direction of movement of the bone cement exiting from the aperture in the cannula tip can be controlled in this way. The aperture can be positioned by rotating the cannula via the handling elements such that the exiting material flows in the desired direction. With cannulae having a central aperture, such as are known from the prior art, the bone cement, however, always exists forwardly in a longitudinal direction so that the direction of exit cannot be altered by rotating the cannula.

Further advantageous embodiments of the invention are given in the dependent claims.

The invention is described in more detail in the following by way of an embodiment with reference to the drawings, in which are shown.

DESCRIPTION OF DRAWINGS

DETAILED DESCRIPTION

Figure 1:
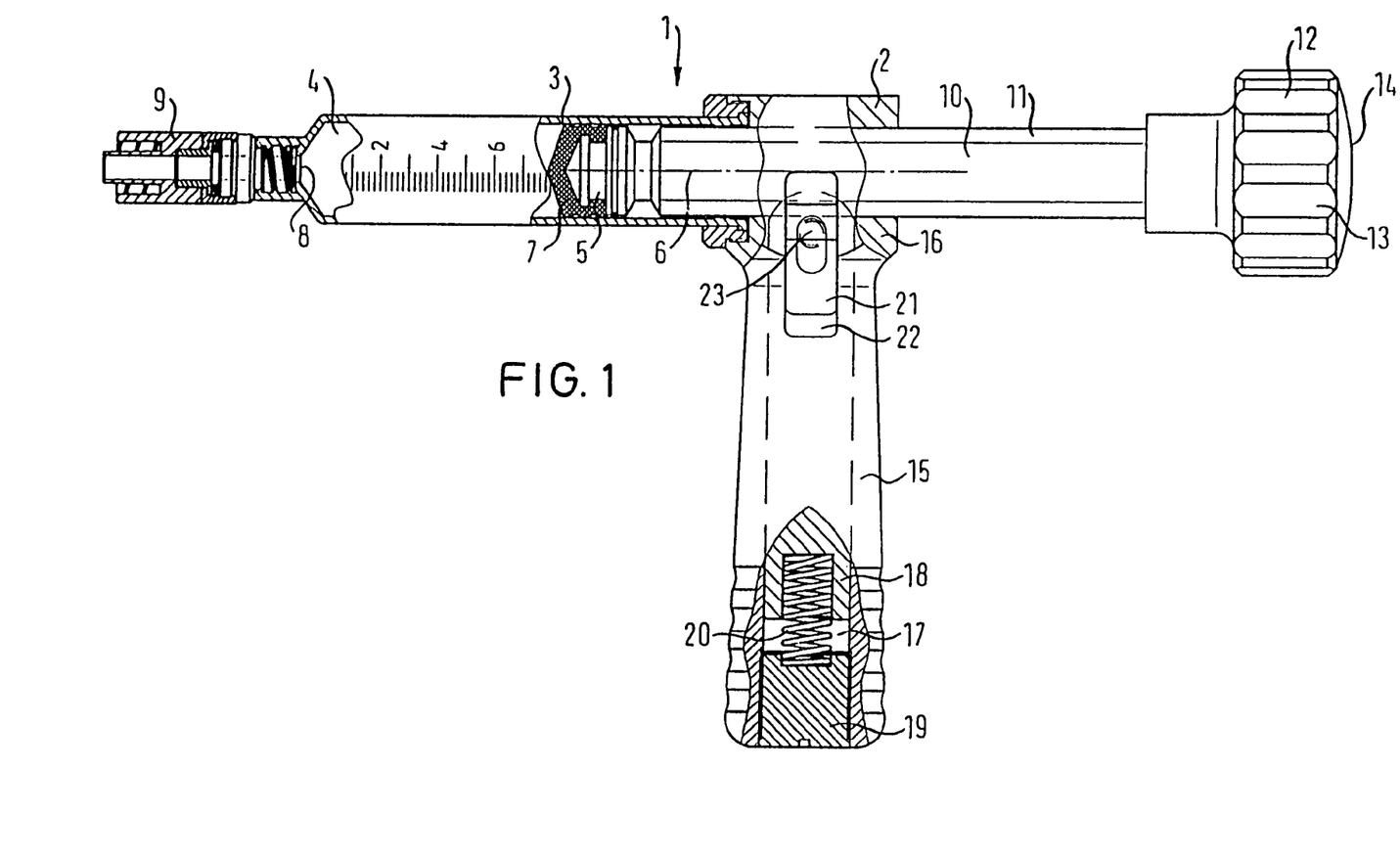
FIG. 1 a partly cut-open cross-section of an application apparatus formed in accordance with the invention.

FIG. 1 shows a pistol-like application apparatus 1 having a housing 2 whose central region is formed as a cylinder 3 for the reception of bone cement at its inside 4. A piston 5 is displaceably supported in the direction of its longitudinal axis 6 inside the cylinder 3, with the piston 5 being sealed with respect to the inner wall of the cylinder 3 by a sealing means 7. An exit aperture 8 is formed at the distal end of the cylinder 3 and coupling element 9, formed for example as a large Luer lock connection, is provided thereat for the coupling of a cannula.

The piston 5 is formed in one piece with an elongated shaft 10 which is provided to form an engaging section with a screw thread 11 at its outer side. An actuating element 12, formed as a turning/sliding knob, is provided at the proximal end of the shaft 10 and has recesses 13 at its peripheral surface and an arched contact surface 14 at its end face.

The housing 2 further comprises a section extending downwardly in FIG. 1 and forming a handle 15, by means of whose upper region 16 the shaft 10 of the piston 5 is led through and which comprises a hollow space 17 in which a locking element 18 is arranged in a longitudinally displaceable manner.

The hollow space 17 is formed to be open with respect to the free end of the handle 15 and is closed there with a closing element 19, for example screwed in. The closing element 19 simultaneously serves as a support element for a coil spring 20 with which the locking element 18 is forced into the direction of the upper region 16 of the handle 15 so that it comes into contact with shaft 10 of the piston 5.

An unlocking element 21 formed as a slider is connected to the locking element 21 and is displaceably guided in a guide recess 22 at the outer side of the housing 2. The unlocking element is connected to the locking element 18 via a bolt 23 such that when the unlocking element 21 is displaced in the direction of the free end of the handle 15, the locking element 18 is displaced against the spring force of the spring 20.

Figure 2:
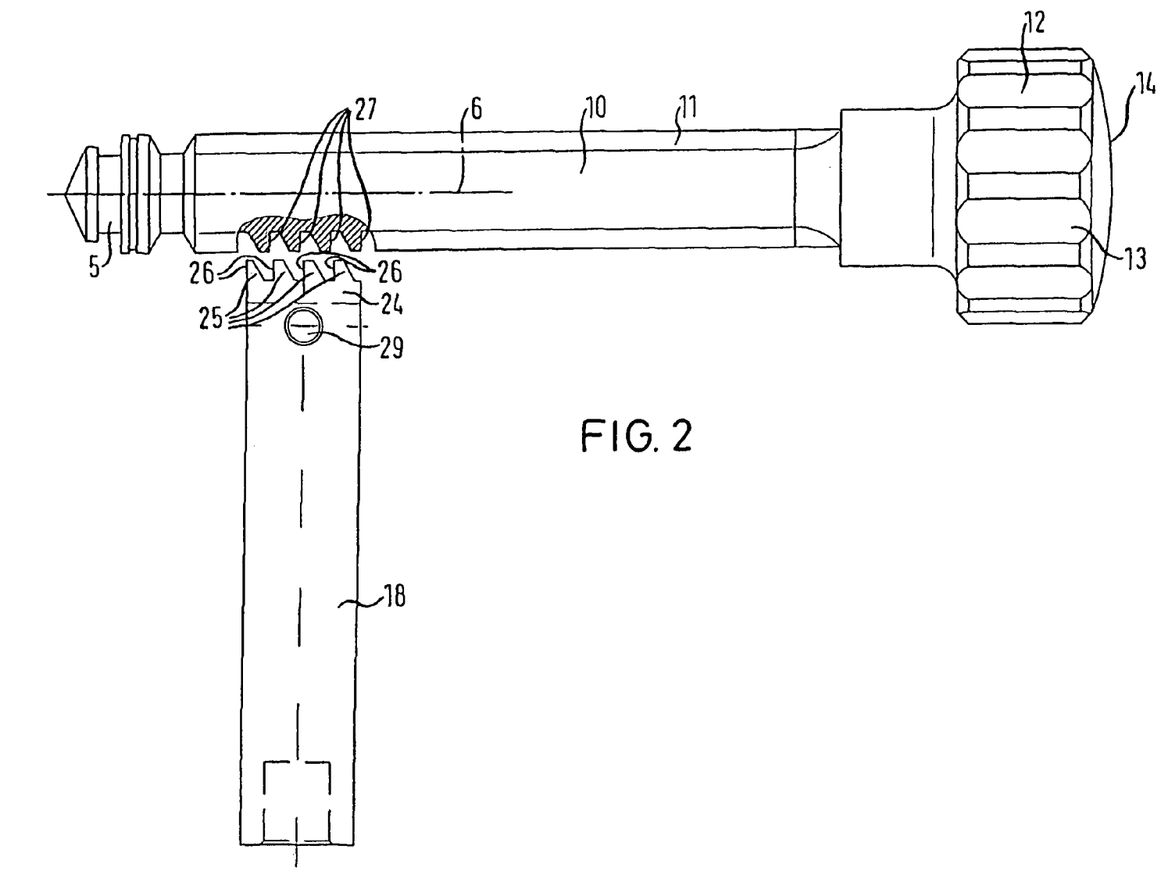
FIG. 2 a detailed view of an apparatus of FIG. 1.

The cooperation of the locking element 18 with the shaft 10 of the piston 5 is shown more clearly in FIG. 2.

It can be seen in FIG. 2, that the end of the locking element 18 disposed toward the shaft 10 is formed as a rack 24 whose teeth 25 form a cooperating toothed arrangement for the screw thread 11 of the shaft 10.

If the unlocking element 21 is displaced downwardly to the free end of the handle 15, then the locking element 18 is displaced downwardly against the force of the spring 20 via the bolt 23 until the locking element 18 and the shaft 10 are uncoupled, as is shown in FIG. 2. In this state, the shaft 10, and thus the piston 5, can be substantially freely displaced directly in the longitudinal direction in the cylinder 3 by, for example, pressing the palm of the hand on the contact surface 14. This displaceability is slightly impaired only by the friction present between the sealing means 7 and the inner wall of the cylinder 3.

If the unlocking element 21 is released again, the locking element 18 is forced in the direction of the shaft 10 by the force of the spring 20 until the teeth 25 of the rack 24 come into engagement with the screw thread 11 of the shaft 10. In this state, a longitudinal displacement of the shaft 10, and thus of the piston 5, is only possible by a screwing of the shaft 10, with this preferably being carried out via the actuating element 12 formed as a screw head. While, in this state, only a relatively slight advance of the piston 5 is carried out by the screw movement in each case, the pressure which can be applied to the bone cement arranged at the inside 4 of the cylinder 3 by the screw movement is, however, substantially higher than can be generated by a direct displacement in the longitudinal direction of the shaft 10 with the shaft 10 uncoupled from the locking element 18.

As can be seen from FIG. 2, the flanks 26, 27 of the screw thread 11 or the teeth 25, which contact one another during the screwing of the piston 5 into the cylinder 3, are formed to extend substantially perpendicular to the longitudinal axis 6. It is thus achieved that the high pressure forces created between the flanks 26 and 27 during the screwing of the piston are fully absorbed without a force component acting on the flanks 27 in a direction perpendicular to the longitudinal axis which could effect a displacement of the locking element 18 against the force of the spring 20. An unwanted uncoupling of the locking element 18 from the shaft 10 is thus excluded even when a very high pressure arises.

Figure 3:
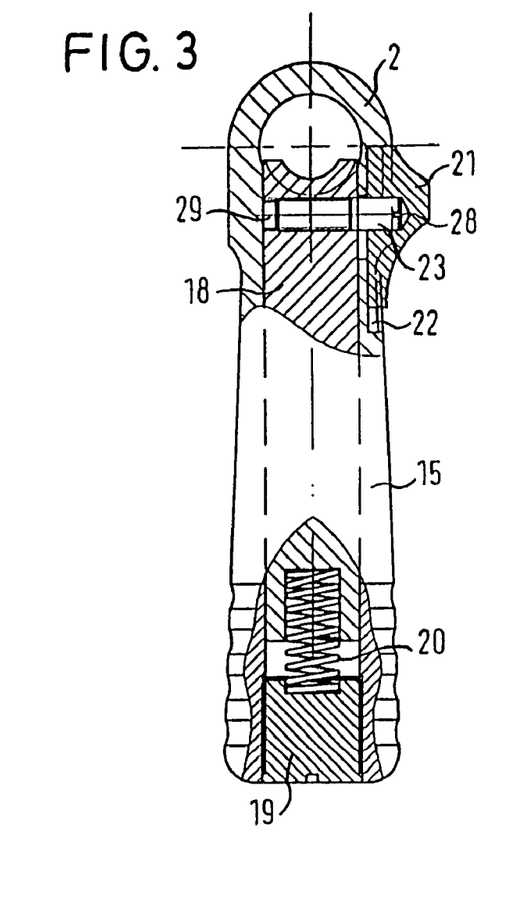
FIG. 3 a partly cut-open cross-section of the apparatus of FIG. 1.

It can be seen from the part cross-section of FIG. 3 that the teeth 25 of the rack 24 are formed in part-annular shape in cross-section and thus create an enlarged contact region with respect to the screw thread 11. It is thereby ensured that the force occurring between the teeth 25 and the screw thread 11 is spread over the largest possible area so that a breaking out of the teeth 25 or the screw thread 11 is avoided.

Furthermore, the coupling of the locking element 18 with the unlocking element 21 via the bolt 23 can be seen in FIG. 3. Both the unlocking element 21 and the locking element 18 have one bore 28, 29 each for this purpose into which the respective end of the bolt 23 engages. In this way, a direct coupling is created between the unlocking element 21 and the locking element 18.

Figure 4:
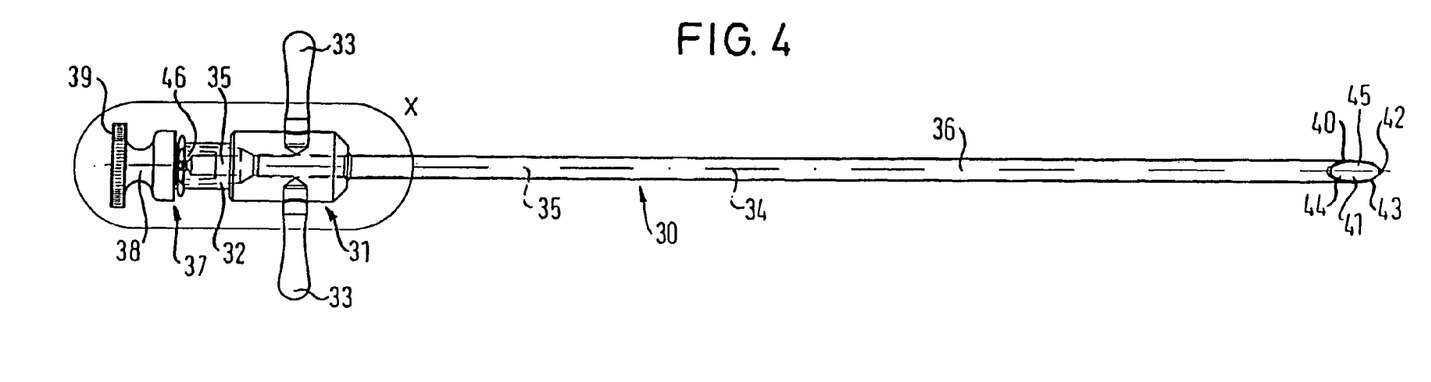
FIG. 4 a cannula formed in accordance with the invention.

FIG. 4 shows a cannula formed in accordance with the invention which can, for example, be connected to an apparatus in accordance with FIG. 1. The cannula 20 has a coupling element 32 at its proximal end 31 for this purpose which is formed, for example, as a large Luer lock connection and which can be sealingly connected to the corresponding coupling element 9 (see FIG. 1). The coupling element is made, for example, of metal in order to be able to absorb the forces which occur when the cannula is driven in.

Two pin-like handling elements 33, which extend radially outwardly, are provided at the proximal end 31 of the cannula 30 and the inserted cannulae 30 can both be turned simply around their longitudinal axis 34 and simply pulled back out of the body of the patient again in the direction of the longitudinal axis 34 via these.

Furthermore, a mandrin 35 is shown in FIG. 4 which is inserted in the tube 36 of the cannula 30 and which comprises a closing element 38 at its proximal end 37. The closing element 38 can be used, on the one hand, to hold the mandrin 35 during insertion into and removal from the cannula 30 and, on the other hand, to position the cannula 30 at the desired position using a driving means, for example, a hammer, if required. The end face of the closing element 38 is formed as an impact surface 39 for this purpose.

An aperture 41 is provided at the distal end 40 of the cannula 30 which can be generated, for example, by an oblique cut of the tube 36. The distal end 40 of the cannula 30 is formed asymmetrically with respect to its longitudinal axis 34 by this oblique cut, with in particular the tip 42 of the cannula 30 coming to rest to the side of the longitudinal axis 34, i.e. at a plane behind the longitudinal axis 34 in the representation of FIG. 4.

The edge 43 of the tube 36 forming the border of the aperture 41 is ground such that this edge 43 forms a cutting edge.

The mandrin 35 is likewise formed with an oblique cut at its distal end and arranged inside the cannula 30 such that the corresponding oblique surface 44 coincides with the likewise obliquely arranged exit area 45 of the aperture 41. To ensure this coincidence, an adjusting unit is provided at the proximal end 37 of the mandrin 35 in the form of a pin 46 which engages into a corresponding recess at the coupling element 32 and thus forms rotational security between the mandrin 35 and the cannula 30.

Figure 5:
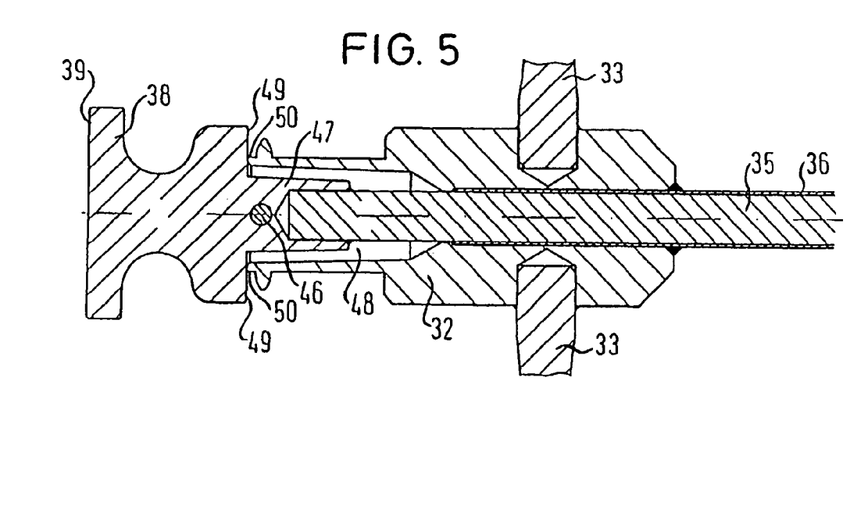
FIG. 5 a detailed view of the cannula of FIG. 4.

The pin 46 can be seen in more detail in the detailed representation of FIG. 5. The arrangement of the mandrin 35 inside the tube 36 of the cannula 30 can likewise be seen from this representation.

The closing element 38 has a lug 47 which engages in a hollow space 48 in the coupling element 32, the diameter of the lug 47 being lower than the clearance of the hollow space 48 so that no jamming of the closing element 38 and thus of the mandrin 35 with the coupling element 32 can take place despite the high impact forces even when the cannula 30 is driven in with a hammer. It is thereby ensured that the mandrin 35 can be removed without problem after the cannula 30 has been positioned.

The closing element 38 is supported at the end face 50 of the coupling element 32 via a support surface 49 to transmit the impact forces hitting the impact surface 39 of the closing element 38 to the cannula 30.

Figure 6:
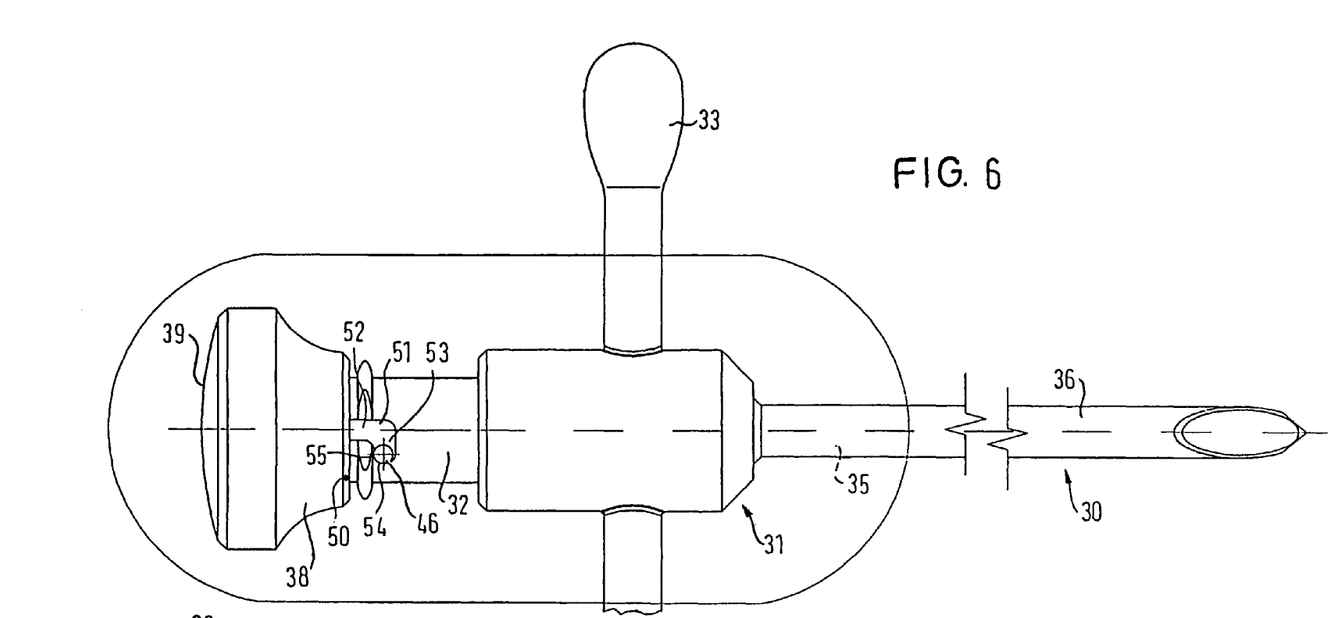
FIG. 6 a further embodiment of a cannula formed in accordance with the invention.
Figure 7:
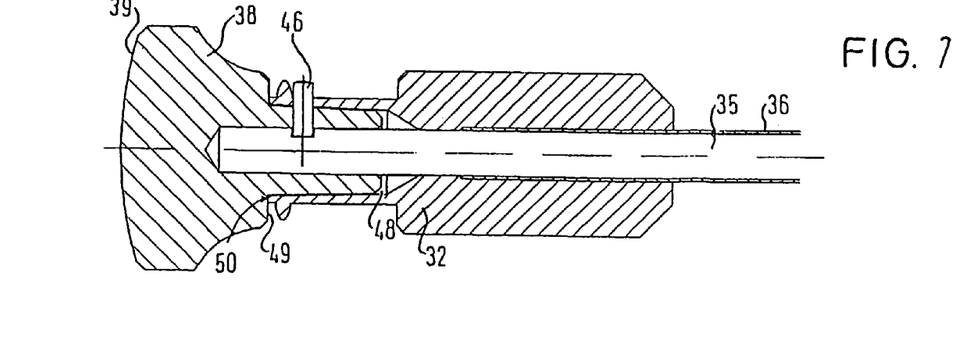
FIG. 7 a detailed view of the cannula of FIG. 6.

While the recess for the pin 46 can generally be formed, for example, as a straight slot extending in the axial direction of the cannula 30, the recess in FIGS. 6 and 7 is formed as an angled or L-shaped slot 51. The slot 51 comprises a longitudinal section 52, which extends in the axial direction of the cannula 30 and which forms the open end of the slot 51 at the annular front surface 50 of the coupling element 32, and a cross-section 53 which extends in the peripheral direction of the coupling element 32 and which is arranged substantially perpendicular to the longitudinal section 52.

The slot 51 forms a bayonet fastening together with the pin 46, with a recess being provided in the form of a latch cutout 55 disposed towards the front face 50 of the coupling element 32 in the region of the free end 54 of the slot 51 and with the pin 46 coming to rest in full or in part therein, depending on the depth of the latch cutout 55, when the bayonet fastener is closed. In this way, rotational security of the mandrin 35 is ensured with respect to the cannula 30 despite the cross-section 53 extending in the peripheral direction of the coupling element 32.

The application apparatus 1 in accordance with the invention and the cannula formed in accordance with the invention are used as follows:

The cannula 30 is first introduced into the body of the patient together with the inserted mandrin 35, with this being done with the aid of a hammer where required. In the embodiment of FIGS. 6 and 7, the coupling between the mandrin 35 and the cannula 30 is made via the bayonet fastening formed by the pin 46 and the slot 51. The bayonet fastening prevents the mandrin 35 from being forced back and partly exiting the cannula 30 due to a spring effect of the mandrin 35 when the cannula 30 is driven in. The mandrin 35 could be forced so far back without an appropriate security that the pin 46 would leave its longitudinal guide and that thereby the rotational security would no longer apply between the mandrin 35 and the cannula 30.

The respective position of the cannula 30 is tracked during the introduction on a CT (computer tomograph) for example. If the position of the distal end 40 of the cannula 30 deviates from the desired position, the cannula 30 is turned via the handling elements 33 so that the tip 42 comes to lie in the direction of the desired position. In a further introduction of the cannula 30, a desired migration of this tip 42 in the direction of the desired position will take place due to the asymmetrical tip 42.

When the cannula 30 is correctly positioned, the mandrin 35 is gripped via the closing element 38 and optionally pulled out of the cannula 30 after the release of the bayonet fastening.

The bone cement used is subsequently mixed and sucked into the inside 4 of the cylinder 3 via a loading cannula connected to the coupling element 9 of the application apparatus 1. The unlocking element is downwardly displaced against the force of the spring 20 for this purpose so that the teeth 25 disengage from the screw thread 11 so that the bone cement is sucked into the cylinder 3 via the loading cannula by a simple pulling back of the piston 5 with the shaft 11.

The loading cannula is subsequently separated from the application device 1 and the latter is connected to the injection cannula 30 in accordance with the invention which has already been positioned.

In the next process step, again with an uncoupled locking element 18, the piston 5 is pushed directly into the cylinder 1 with the shaft 10 by pressure loading of the contact surface 14 of the actuating element 12, whereby the cement material arranged at the inside 4 of the cylinder 3 is injected into the bone via the cannula 30. A constantly increasing pressure is built up by the injection into the bone material until said pressure is finally so high that a further application of the bone cement by pressing onto the contact surface 14 is no longer possible.

At this point in time, the unlocking element 21 is released so that the locking element 18 is displaced in the direction of the shaft 10 by the force of the spring 20 until the teeth 25 are in engagement with the screw thread 11.

The pressure at the inside 4 of the cylinder 3 can subsequently be further increased by turning the shaft 10 via the actuating element 12 so that the piston 5 is slowly further displaced into the inside of the cylinder 1. If it is recognized, for example by observation at a fluoroscope, that the applied bone cement is flowing in an unwanted direction, this direction of flow can be changed, for example, by the cannula 30 being rotated via the handling elements 33 such that the aperture is disposed in the desired direction.

If the quantity of bone cement exiting the aperture 41 is too high due to the high pressure, then this pressure can be reduced immediately by a displacement of the unlocking element 21 and the uncoupling and release which thereby takes place of the shaft 10 and the piston 5 connected thereto. It is prevented in this manner that the bone cement is applied to dangerous points inside the body.

The pressure can subsequently be built up again, first by direct displacement and subsequently, as described, by a further screw movement after a reorientation of the cannula 30, for example, by turning via the handling elements 33.

After the full application of the bone cement, the application apparatus 1 can be separated from the cannula 30.

After hardening, the cannula 30 can subsequently be easily tilted and simultaneously turned around its longitudinal axis 34 with the aid of the handling elements 33, with a shearing off of the hardened bone cement still located inside the tube 36 taking place due to the oblique, ground edge 43 so that this material is reliably removed from the body together with the cannula 30 when the cannula 30 is subsequently pulled out.

REFERENCE NUMERAL LIST 1 application device
2 housing
3 cylinder
4 inside of the cylinder
5 piston
6 longitudinal axis
7 sealing means
8 exit aperture
9 coupling element
10 shaft
11 screw thread
12 actuating element
13 recesses
14 contact surface
15 handle
16 upper region of the handle
17 hollow space
18 locking element
19 closing element
20 coil spring
21 unlocking element
22 guide cutout
23 bolt
24 rack
25 teeth of the rack (cooperating toothed arrangement)
26 flanks
27 flanks
28 bore
29 bore
30 cannula
31 proximal end of the cannula
32 coupling element
33 handling elements
34 longitudinal axis of the cannula
35 mandrin
36 tube
37 proximal end of the mandrin
38 closing element
39 impact surface
40 distal end of the mandrin
41 aperture
42 tip
43 edge
44 oblique surface
45 exit surface
46 pin
47 lug
48 hollow space
49 support surface
50 end face of the coupling element
51 slot
52 longitudinal section
53 cross-section
54 free end of the slot 51
55 latch cutout

The invention claimed is:

1. An apparatus for application of bone cement comprising:
a housing having a cylinder for receiving the bone cement and having a piston arranged in a longitudinally displaceable manner in the cylinder by which the bone cement can be pressed out through an exit aperture formed in the cylinder;
a screw movement for longitudinally displacing the piston in the cylinder for the application of the bone cement under high pressure; and
an arrangement for switching between the displacement of the piston by the screw movement and a direct displacement in the longitudinal direction without a screw movement, the arrangement including a biasing spring and a cooperating toothed arrangement,
wherein said screw movement comprises an engaging thread section having a screw thread, the biasing spring resiliently pushing the cooperating toothed arrangement in a linear direction perpendicular to the longitudinal movement of the piston into releasable engagement with the engaging thread section such that the longitudinal displacement of the piston is effected when the engaging thread section is turned, and engagement of the engaging thread section and cooperating toothed arrangement being resiliently released when biasing of the spring is released to lineally move the cooperating toothed arrangement away from the engaging thread section in a direction perpendicular to the longitudinal movement of the piston and without a movement of the cooperating toothed arrangement in the direction of the longitudinal movement of the piston.

2. An apparatus in accordance with claim 1, wherein the cooperating toothed arrangement is formed as a rack.

3. An apparatus in accordance with claim 1, wherein the cooperating toothed arrangement grips around the screw thread regionally.

4. An apparatus in accordance with claim 1, wherein the piston can be longitudinally displaced in a substantially free manner in the cylinder when the screw movement is unengaged.

5. An apparatus in accordance with claim 1, wherein the screw movement has a distal and proximate end and the screw movement has a longitudinal axis having an upstream ray extending toward the proximate end and a downstream ray extending toward the distal end and wherein tooth flanks of the cooperating toothed arrangement and/or flanks of the engaging thread section of the screw movement, which contact one another during the application of the bone cement under pressure, form an angle of approximately 90° with the upstream ray of the longitudinal axis of the engaging thread section and which longitudinal axis extends parallel to the direction of displacement.

6. An apparatus in accordance with claim 1, wherein the piston and the engaging thread section are formed as one piece.

7. An apparatus in accordance with claim 1, wherein the piston and the engaging thread section are formed as separate parts which are connected to one another and which are rotatable with respect to one another.

8. An apparatus in accordance with claim 1, wherein the cylinder comprises a circular cylinder.

9. An apparatus in accordance with claim 1, wherein a cannula can be fastened to the exit aperture of the cylinder.

10. An apparatus in accordance with claim 9 wherein the cannula is effective for application of bone cement into bone.

11. An apparatus for an application of bone cement comprising:
a housing having a cylinder for receiving said bone cement and having a piston arranged in a longitudinally displaceable manner in the cylinder by which the bone cement can be pressed out through an exit aperture formed in the cylinder;
a screw movement having a distal and proximate end and for longitudinally displacing the piston in the cylinder for the application of the bone cement through the exit aperture at the distal end under high pressure, the screw movement having a longitudinal axis having an upstream ray extending toward the proximate end and a downstream ray extending toward the distal end; and an arrangement for switching between the displacement of the piston by the screw movement and a direct displacement in the longitudinal direction without a screw movement, the arrangement including a biasing spring and a cooperating toothed arrangement, wherein said screw movement comprises an engaging thread section having a screw thread, the biasing spring resiliently pushing the cooperating toothed arrangement in a linear direction perpendicular to the longitudinal movement of the piston into releasable engagement with the engaging thread section such that the longitudinal displacement of the piston is effected when the engaging thread section is turned, and engagement of the engaging thread section and cooperating toothed arrangement being resiliently released when biasing of the spring is released to lineally move the cooperating toothed arrangement away from the engaging thread section in a direction perpendicular to the longitudinal movement of the piston and without a movement of the cooperating toothed arrangement in the direction of the longitudinal movement of the piston, and wherein at least one of tooth flanks of the cooperating toothed arrangement, or tooth flanks of the engaging thread section of the screw movement, which contact one another during the application of the bone cement under pressure, form an angle of about 90° with the upstream ray extending toward the proximate end of the longitudinal axis of the engaging section of the screw movement which extends parallel to the direction of displacement.

12. An apparatus for an application of bone cement comprising:

a housing having a cylinder for receiving said bone cement and having a piston arranged in a longitudinally displaceable manner in the cylinder by which the bone cement can be pressed out through an exit aperture formed in the cylinder;

a screw movement having a distal and proximate end and which screw movement is effective for longitudinally displacing the piston in the cylinder for the application of the bone cement under high pressure, the screw movement having a longitudinal axis having an upstream ray extending toward the proximate end and a downstream ray extending toward the distal end;

a cannula which is effective for the application of bone cement at the distal end of the screw movement; and an arrangement for switching between the displacement of the piston by the screw movement and a direct displacement in the longitudinal direction without a screw movement, the arrangement including a cooperating toothed arrangement, a handle with a chamber and a biasing spring in the chamber of the handle, wherein said screw movement comprises a longitudinal engaging thread section having a screw thread that engages the cooperating toothed arrangement provided at the housing such that the longitudinal displacement of the piston is effected when the engaging thread section is turned, the cooperating toothed arrangement being pushed by the biasing spring against the engaging thread section in a linear direction perpendicular to the direction of displacement of the piston, and engagement of the engaging thread section and cooperating toothed arrangement being resiliently released when the biasing of the spring is released to lineally move the cooperating toothed arrangement away from the engaging thread section in a direction perpendicular to the longitudinal movement of the piston, and wherein faces of tooth flanks of the cooperating toothed arrangement, and of the engaging thread section of the screw movement, contact one another during the application of the bone cement under pressure, and each face form an angle of about 90° with the upstream ray extending toward the proximate end of the longitudinal axis of the engaging section extending parallel to the direction of displacement.

13. An apparatus for application of bone cement comprising:

a housing having a cylinder for receiving said bone cement and having a piston arranged in a longitudinally displaceable manner in the cylinder by which the bone cement can be pressed out through an exit aperture formed in the cylinder;

a screw movement having a distal and proximate end and which screw movement is effective for longitudinally displacing the piston in the cylinder for the application of the bone cement under high pressure, the screw movement having a longitudinal axis having an upstream ray extending toward the proximate end and a downstream ray extending toward the distal end; and an arrangement for switching between the displacement of the piston by the screw movement and a direct displacement in the longitudinal direction without a screw movement, the arrangement including a cooperating toothed arrangement, a handle with a chamber and a biasing spring in the chamber of the handle, wherein said screw movement comprises an engaging thread section having a screw thread that engages a cooperating toothed arrangement under resilient bias provided by the biasing spring pushing in a direction perpendicular to the'longitudinal displacement of the piston such that the longitudinal displacement of the piston is effected when the engaging section is turned, the cooperating toothed arrangement being pressed by the biasing spring against the engaging thread section in a direction perpendicular to the direction of displacement of the piston, and engagement of the engaging thread section and cooperating toothed arrangement being resiliently released when the biasing of the spring is released to lineally move the cooperating toothed arrangement away from the engaging thread section in a direction perpendicular to the longitudinal movement of the piston, and wherein tooth flanks of the cooperating toothed arrangement and tooth flanks of the engaging thread section of the screw movement, which contact one another during the application of the bone cement under pressure, form an angle of about 90° with the upstream ray extending toward the proximate end of the longitudinal axis of the engaging section of the screw movement which extends parallel to the direction of displacement.

14. The apparatus in accordance with claim 11, wherein the apparatus further includes a handle portion extending from the cylinder, the handle portion housing the biasing spring which resiliently biases the cooperating toothed arrangement against the engaging thread section.

15. An apparatus for the application of bone cement comprising:

a longitudinal cylinder for receiving the bone cement;

a piston arranged in a longitudinally displaceable manner in the cylinder for pressing the bone cement longitudinally through the cylinder through an exit aperture formed in the cylinder;

a handle extending from the cylinder, the handle including a chamber and a biasing spring in the chamber of the handle;

a screw which has a longitudinal body having a distal and proximate end, the screw extending down the cylinder, the screw including a longitudinal engaging thread section with a screw thread on the longitudinal body, the screw connected to the piston for longitudinally displacing the piston in the cylinder for the application of the bone cement under high pressure, the screw having a longitudinal axis having an upstream ray extending toward the proximate end and a downstream ray extending toward the distal end;

an arrangement for switching between the displacement of the piston by the screw movement and a direct displacement of the piston in the longitudinal direction without a screw movement, the arrangement including the engaging thread section and a cooperating toothed arrangement which moves to engage the engaging thread section for effecting high pressure movement of the bone cement through the chamber, the cooperating toothed arrangement being pressed by the biasing spring against the engaging thread section, the biasing spring linearly pushing the cooperating toothed arrangement into engagement with the engaging thread section in a direction perpendicular to the direction of displacement of the piston, and engagement of the engaging thread section and cooperating toothed arrangement being resiliently released when the biasing of the spring is released to lineally move the cooperating toothed arrangement away from the engaging thread section in a direction perpendicular to the longitudinal movement of the piston, the cooperating toothed arrangement including tooth flanks and the thread engaging section including tooth flanks, wherein tooth flanks of the cooperating toothed arrangement and tooth flanks of the engaging thread section of the screw which contact one another during the application of the bone cement under pressure form an angle with the upstream ray extending toward the proximate end of the longitudinal axis of the screw which is approximately 90°; and a cannula at the distal end of the cylinder, the cannula effective for application of bone cement into bone.

* * * * *